US011446364B2

(12) United States Patent
Shi et al.

(10) Patent No.: US 11,446,364 B2
(45) Date of Patent: *Sep. 20, 2022

(54) STABLE THERMOLYSIN HYDROGEL (71) Applicant: SMITH & NEPHEW, INC., Memphis, TN (US)

(72) Inventors: Lei Shi, Mansfield, TX (US); Aleksa Jovanovic, Fort Worth, TX (US); Dennis Carson, Burleson, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 787 days.

This patent is subject to a terminal disclaimer.

(21) Appl. No.: 14/441,135

(22) PCT Filed: Nov. 14, 2013

(86) PCT No.: PCT/US2013/070171
§ 371 (c)(1),
(2) Date: May 6, 2015

(87) PCT Pub. No.: WO2014/078581
PCT Pub. Date: May 22, 2014

(65) Prior Publication Data
US 2015/0283217 A1    Oct. 8, 2015

Related U.S. Application Data

(60) Provisional application No. 61/726,175, filed on Nov. 14, 2012.

(51) Int. Cl.
*A61K 38/48*     (2006.01)

(52) U.S. Cl.
CPC .. *A61K 38/4886* (2013.01); *C12Y 304/24027* (2013.01)

(58) Field of Classification Search
None
See application file for complete search history.

(56) References Cited

U.S. PATENT DOCUMENTS 4,228,277 A * 10/1980 Landoll ................. C08B 11/193
536/88
5,145,681 A    9/1992 Fortney et al. ............ 424/94.63
(Continued)

FOREIGN PATENT DOCUMENTS

| CN | 1929826 | 3/2007 |
|----|---------|--------|
| CN | 102573760 | 7/2012 |

(Continued)

OTHER PUBLICATIONS

Lin et al., Hydrogels in controlled release formulations: Network design and mathematical modeling, Advanced Drug Delivery Reviews 58 (2006) 1379-1408.*

(Continued)

*Primary Examiner* — Erin M. Bowers
(74) *Attorney, Agent, or Firm* — Norton Rose Fulbright US LLP (57) ABSTRACT

Disclosed is a hydrogel comprising a hydrophilic gelling agent that includes a nonionic cellulose ether, and active thermolysin, wherein the proteolytic activity of the thermolysin does not decrease by more than 20% when stored at room temperature for 6 months.

21 Claims, 3 Drawing Sheets

(56) References Cited

U.S. PATENT DOCUMENTS

| | | | |
|---|---|---|---|
| 5,739,023 A | 4/1998 | Harada et al. | 435/188 |
| 6,235,893 B1* | 5/2001 | Reibert | C08B 11/02 264/140 |
| 6,518,054 B1 | 2/2003 | Van den Burg et al. | 435/219 |
| 6,548,556 B2 | 4/2003 | Hobson et al. | 514/772.4 |
| 7,785,584 B2 | 8/2010 | Jones et al. | 424/94.65 |
| 8,163,298 B2 | 4/2012 | Griffiths-Brophy et al. | 424/400 |
| 9,045,743 B2 | 6/2015 | Hoelke et al. | |
| 10,058,596 B2 | 8/2018 | Hanson | |
| 2003/0008830 A1 | 1/2003 | Prozillo | 514/9.4 |
| 2003/0198631 A1 | 10/2003 | Shi et al. | 424/94.63 |
| 2004/0028739 A1 | 2/2004 | Rippon et al. | |
| 2004/0151765 A1 | 8/2004 | Ritchie et al. | 424/445 |
| 2008/0124381 A1* | 5/2008 | Barnhart | A61K 8/0208 424/443 |
| 2008/0152698 A1 | 6/2008 | Effing et al. | |
| 2009/0010910 A1 | 1/2009 | Toren et al. | 424/94.2 |
| 2010/0021416 A1* | 1/2010 | Lichter | A61K 9/0046 424/78.17 |
| 2010/0159564 A1 | 6/2010 | Dwulet et al. | 435/220 |
| 2011/0190722 A1 | 8/2011 | Munro et al. | 604/367 |
| 2013/0045196 A1 | 2/2013 | Shi et al. | 424/94.64 |
| 2014/0154235 A1 | 6/2014 | Shi et al. | 424/94.64 |

FOREIGN PATENT DOCUMENTS

| | | |
|---|---|---|
| GB | 2147206 A | 5/1985 |
| JP | 2006-503044 | 1/2006 |
| JP | 2007-500673 | 1/2007 |
| WO | WO 2006/037606 | 4/2006 |
| WO | 2011-507920 | 3/2011 |
| WO | WO 2011/071986 | 6/2011 |
| WO | WO 2012/155027 | 11/2012 |
| WO | WO 2013/170128 | 11/2013 |

OTHER PUBLICATIONS

Office Action issued in Japanese Application No. 2015-542048, dated Sep. 11, 2017 (with English translation).
Ashland Product Data "Natrosol™ 250 Water Soluble Hydroxyethylcellulose," Ashland Specialty Ingredients, 2015.
Ashland Physical Chemical Property Book, "Klucel™ hydroxypropylcellulose Physical and Chemical Properties," 2017.
Milne, C.T., et al., "A comparison of collagenase to hydrogel dressings in wound debridement", *Wounds* 2010, vol. 22, No. 11, Retrieved from https://www.woundsresearch.com/content/comparison-collagenase-hydrogel-dressings-wound-debridement. Accessed Jun. 12, 2020, 5 pages.
Office Action issued in corresponding Canadian Application No. 2,890,757, dated May 11, 2020.

* cited by examiner

STABLE THERMOLYSIN HYDROGEL

CROSS REFERENCE TO RELATED APPLICATIONS

This application is a national phase application under 35 U.S.C. § 371 of International Patent Application No. PCT/US2013/070171 filed Nov. 14, 2013, which claims the benefit of U.S. Provisional Application No. 61/726,175, filed Nov. 14, 2012. The contents of the referenced applications are incorporated into this specification by reference.

BACKGROUND OF THE INVENTION

A. Field of the Invention

The invention generally relates to methods and compositions useful for treating wounds with a hydrogel that includes active thermolysin and a nonionic cellulose ether as the gelling agent.

B. Description of Related Art

The presence of eschar and other necrotic tissue in a wound can impede the healing process, causing the wound to become a slow-healing or "chronic" wound. Diabetic foot ulcers, venous leg ulcers, arterial leg ulcers, decubitus ulcers, stasis ulcers, dermal ulcers, burns, and pressure ulcers are examples of such wounds.

Enzymatic wound debridement agents can be used to digest eschar and other necrotic tissue, thereby facilitating the healing process of wounds. Such agents are enzymes that can digest eschar and other necrotic tissue. The majority of wound debriding agents, including thermolysin, are in environments that shield the agent from water such as gels, creams, and ointments. The reason for this is to preserve the stability of the debriding agent, as such agents tend to have limited stability in aqueous environments (U.S. Publication 2003/0198631). For instance, all of the example formulations in U.S. Publication 2003/0198631 concern creams and non-aqueous gels. Ironically, however, debriding agents such as thermolysin are most active in aqueous environments. This explains the use of oil-in-water emulsions (such as creams) as delivery vehicles for thermolysin.

SUMMARY OF THE INVENTION

The inventors have solved the stability issues seen with the use of thermolysin in aqueous environments. In particular, the inventors have discovered a way to stabilize thermolysin in an aqueous environment by using a nonionic cellulose ether to create a hydrogel that contains thermolysin. A hydrogel is a gel in which water is the continuous phase or medium. Hydrogels are typically in a semi-solid dosage form. The combination of the cellulose ether/water/thermolysin produces a surprising stable formulation that can be used to treat wounds. For instance, data confirms that such a hydrogel can be stored at room temperature (about 20-25° C.) for 24 months and still retain at least 80% or 90% of its original activity of thermolysin (i.e., the activity of thermolysin does not decrease by more than 20% or 10%). This stability is surprising because proteases such as thermolysin are expected to be highly unstable and quickly degraded in an aqueous environment such as a hydrogel. In fact, this stability is even higher than some non-aqueous vehicles, creams, and the like, which is even more surprising, as such vehicles were traditionally thought to offer thermolysin additional stability protection from aqueous environments.

In one instance, there is disclosed a hydrogel comprising a hydrophilic gelling agent that includes a nonionic cellulose ether and active thermolysin, wherein the proteolytic activity of the thermolysin does not decrease by more than 20% or by more than 10% (i.e., retains at least 80 or 90% of its activity) when stored at room temperature for 6, 12, 18, or 24 months. Non-limiting examples of nonionic cellulose ethers are provided throughout this specification—such examples include a hydroxyalkyl cellulose ether (e.g., hydroxyethylcellulose (HEC), hydroxypropylcellulose (HPC), or hydroxypropylmethylcellulose (HPMC), or any combination thereof or all of said cellulose ethers). The amount of nonionic cellulose ether within the hydrogel can vary as needed to achieve a particular viscosity. In certain instances, the amount can range from 0.1 to 30% w/w, or 0.1 to 20% w/w, or 0.1 to 10% w/w, or 0.1 to 5% w/w of the nonionic cellulose ether or can include 0.1, 0.2, 0.3, 0.4, 0.5, 0.6, 0.7, 0.8, 0.9, 1, 2, 3, 4, 5, 6, 7, 8, 9, 10, 15, 20, 25, or 30% w/w. In one embodiment, the amount of hydroxyethylcellulose within the hydrogel can range from 2.5 to 4.5% w/w. In another embodiment, the amount of hydroxypropylcellulose within the hydrogel can range from 0.01 to 10% w/w. In still another embodiment, the amount of hydroxypropylmethylcellulose within the hydrogel can range from 1.5 to 2.5% w/w. Further, the amount of thermolysin within the hydrogel can vary depending on dosing requirements of a given wound. In some aspects, the amount of thermolysin within the hydrogel can range from 0.1 to 5% w/w or 0.5 to 1% w/w or 0.1, 0.2, 0.3, 0.4, 0.5, 0.6, 0.7, 0.8, 0.9, 1, 2, 3, 4, or 5% w/w. Further, the hydrogel of the present invention can further include a buffer. The buffer, in certain aspects, can have a pH range of about 7.0 to 8.0 or 7.1, 7.2, 7.3, 7.4, 7.5, 7.6, 7.7, 7.8, 7.9 or 8. In some embodiments, the buffer can have a pH range of about 7.5. The viscosity of the hydrogel can be modified to meet a desired consistency. In some aspects, the viscosity of the hydrogel can range from 5,000 to 100,000 cps, or 10,000 to 100,000 cps, or 15,000 to 100,000 cps, 30,000 to 80,000 cps, or can be about 5,000, 10,000, 15,000, 20,000, 30,000, 40,000, 50,000, 60,000, 70,000, 80,000, 90,000, or 100,000 or any range therein, as measured with a Brookfield RV Viscometer (spindle 14 with small sample adapter) at 10 rpm at room temperature read at 30 seconds. The hydrogel can also include metal salts. Non-limiting examples of metal salts include sodium chloride and calcium chloride. The hydrogel can be sterile of it can be preserved by the inclusion of preservatives. Non-limiting examples of preservatives include methylparaben, propylparaben, and phenoxyethanol. The hydrogel can also include dionls, triols, and polyols. A non-limiting example of a diol is propylene glycol and a non-limiting example of a triol is glycerin. In one particular aspect, the hydrogel can include sodium chloride, calcium chloride, propylene glycol, methylparaben, and propylparaben. Other additives suitable for use in topical compositions of this nature can be included in the hydrogel. In some aspects, the thermolysin can be suspended or solubilized within the hydrogel. In other aspects, the thermolysin can be partially suspended and partially solubilized within the hydrogel. In some aspects, a portion of the thermolysin within the hydrogel can be solubilized (e.g., less than 50, 40, 30, 20, 10, 5, 1, or 0.5% w/w can be solubilized).

Also disclosed is a method of debriding a wound with any one of the hydrogels of the present invention, wherein the wound is in need of debridement. The wound can be a chronic wound. Examples of chronic wounds that can be treated include diabetic foot ulcers, venous leg ulcers, arterial leg ulcers, decubitus ulcers, stasis ulcers, dermal ulcers, burns, or pressure ulcers. In some instances, the wound can include necrotic tissue. The necrotic tissue can be an eschar.

In a further embodiment, there is disclosed a method for stabilizing thermolysin comprising preparing a hydrogel of the present invention. The data within the specification confirm the surprising stability of thermolysin within said hydrogels of the present invention.

Unless otherwise specified, the percent values expressed herein are weight by weight and are in relation to the total composition.

The term "active thermolysin" means thermolysin which exhibits proteolytic activity.

The term "stable" means the proteolytic activity of the thermolysin retains at least 80% of its activity when stored at room temperature for 6 months.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. Similarly, the term "effective" means adequate to accomplish a desired, expected, or intended result.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the hydrogel's ability to stabilize thermolysin.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Effective wound cleansing and debridement help facilitate the healing process. Devitalized tissue present in a wound bed is undesirable—it serves as a reservoir for bacterial growth, contains elevated levels of inflammatory mediators that promote chronic inflammation at the wound site, and impairs cellular migration. The four most common methods used to debride a wound include surgical, autolytic, enzymatic, and mechanical debridement.

With respect to enzymatic debridement, currently SANTYL® Collagenase Ointment is the only approved enzymatic debriding drug product in the U.S. marketplace. This product is a hydrophobic ointment that utilizes collagenase as the debriding agent. While others have attempted to use different debriding agents and various formulations, one of the problems faced is that of stability. In particular, the instability of debriding agents limits their use to effectively debride wounds.

The inventors have discovered a solution to the instability issues surrounding the debriding agent, thermolysin. In particular, the inventors discovered a way to stabilize thermolysin in an aqueous environment by using a nonionic cellulose ether to create a hydrogel that contains and stabilizes active thermolysin. These and other non-limiting aspects of the present invention are described in the following subsections.

A. Hydrogels

The compositions of the present invention are formulated as hydrogels in that that the continuous medium of the formulation is an aqueous environment that has been gelled with a nonionic cellulose ether. The thermolysin can be suspended or solubilized within the gel. It can also be partially solubilized and partially suspended within the gel. Further, other additives can also be added to the hydrogels of the present invention.

1. Thermolysin

Thermolysin is a thermostable metalloproteinase that cleaves at the N-terminus of the hydrophobic residues leucine, phenylalanine, valine, isoleucine, alanine and methionine. The optimal digestion temperature range is 40-80° C. Thermolysin activity is optimal at pH 5.0-8.5. The term "active thermolysin" means thermolysin which exhibits proteolytic activity. Amano Japan is a manufacturer and supplier of thermolysin. The Amano thermolysin was obtained from a bacterial species called *Bacillus thermoproteolyticus rokko*. The CAS No. for thermolysin is 9073-78-3. The thermolysin used in the Examples of this specification is from Amano.

2. Nonionic Cellulose Ethers

Nonionic cellulose ethers are high-molecular-weight compounds that can be made by replacing the hydrogen atoms of hydroxyl groups in the glucose units of cellulose with alkyl or hydroxylalkyl groups. Non-limiting examples of non-ionic alkyl cellulose ethers include methyl cellulose (MC), ethyl cellulose (EC), and ethyl methyl cellulose (EMC). Non-limiting examples of non-ionic hydroxyalkyl cellulose ethers include hydroxyethyl cellulose (HEC), hydroxylpropyl cellulose (HPC), hydroxymethyl cellulose (HMC), hydroxypropylmethyl cellulose (HPMC), ethylhydroxyethyl cellulose (EHEC), hydroxyethylmethy cellulose (HEMC), methylhydroxyethyl cellulose (MHEC), methylhydroxypropylcellulose (MHPC), and hydroxyethylcarboxymethyl cellulose (HECMC). There are a wide range of commercial sources for each of these cellulose ethers (e.g., Dow Chemical Company (USA), Ashland (USA), Samsung Fine Chemicals (USA)). Additional commercial sources of these nonionic cellulose ethers can be found in the International Cosmetic Ingredient Dictionary and Handbook, $12^{th}$ Edition (2008), volumes 1-3.

3. Additives

In addition to thermolysin, nonionic cellulose ether, and water, the hydrogels can include additional ingredients. For instance, water-soluble solvents such as propylene glycol or other diols can be used. Triols and polyols can also be used in the hydrogels. A non-limiting example of a triol is glycerin. The amount of such solvents can range from 1 to 20% w/w, although more or less can be added to achieve a desired result for the hydrogel. Metal salts such as $NaCl_2$ or $CaCl_2$ can be used as stabilization agents. The amounts of salt can range from 0.01 to 1% w/w, although more or less can be added to achieve a desired result for the hydrogel. Preservatives such as methylparaben, propylparaben, and phenoxyethanol can be used to preserve the hydrogel. The amounts of such preservatives can range from 0.01 to 1% w/w, although more or less can be added to achieve a desired result for the hydrogel. Buffers having an appropriate pH range (e.g., 6.5 to 9 or 7 to 8 or about 7.5) for thermolysin can be used. An example of such a buffer is Tris buffer (10 mM, pH=7.5). The water source for the hydrogel can come from the buffer solution. Therefore, the amount of buffer that can be added is an amount that fills out the formulation (e.g., q.s. to 100%). Further additives can be added to achieve a given tactile property or to add an additional functional aspect to the hydrogel (e.g., agents that can further aid in the wound healing process such as vulnerary agents, antimicrobial agents, anti-inflammatory agents, pain-relieving agents, etc.).

4. Preparation of the Hydrogel

The hydrogels of the present invention can be prepared by mixing propylene glycol and preservatives (e.g., methylparaben and propylparaben) in de-ionized (DI) water or Tris buffer (pH=7.5) at 70° C. Upon solubilization (i.e., clear solution is obtained), the solution can be cooled to room temperature (RT) and a gelling agent (e.g., Hydroxyethylcellulose-HEC) can be added. The mixture can then be stirred until homogeneous (i.e., no visible particles of gelling agent, HEC), thereby forming a hydrogel. The active phase can be made by mixing thermolysin, NaCl and $CaCl_2$ in DI water or Tris buffer (pH=7.5) at appropriate concentrations. Upon homogenization (a white slurry will be obtained), the active phase can then be added to a hydrogel (at appropriate concentration). The final mixture can then be stirred at RT. A milky hydrogel is then obtained.

B. Methods of Using the Hydrogels

The hydrogels of the present invention may be used in a variety of methods. For instance, they can be used to debride wounds such as chronic wound. Such methods include applying to the wound a composition comprising thermolysin (e.g., via topical application). After application, the wound may be covered with a wound dressing such as a gauze pad. The hydrogel may be applied to a dressing such as a gauze pad first and then applied to the wound surface. The application amount depends on the severity and type of the wound and nature of the subject.

In certain aspects, the hydrogel can be applied to the wound periodically, for example, daily, twice daily, once every other day, once a week, as needed. A therapeutic regimen can be used that includes periodic dressing changes with wound cleansing and application of fresh composition between changes until the debridement of the necrotic tissue is complete.

A wide variety of wounds can be treated with the hydrogels of the present invention. Examples include burns, acute wounds, or chronic wounds. Non-limiting examples of chronic wounds include diabetic foot ulcers, venous leg ulcers, arterial leg ulcers, decubitus ulcers, stasis ulcers, dermal ulcers, burns, and pressure ulcers.

C. Kits

Kits are also contemplated as being used in certain aspects of the present invention. For instance, a hydrogel of the present invention can be included in a kit. A kit can include a container. Containers can include a bottle, a metal tube, a laminate tube, a plastic tube, a dispenser, a pressurized container, a barrier container, a package, a compartment, or other types of containers such as injection or blow-molded plastic containers into which the hydrogels are retained. The kit can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. The containers can be designed for single-dose or multiple-dose dispensing. A kit can also include instructions for using the kit and/or compositions.

Further, the hydrogels of the present invention may also be sterile, and the kits containing such hydrogels can be used to preserve the sterile hydrogel. The hydrogels may be sterilized via an aseptic manufacturing process or sterilized after packaging by methods known in the art.

EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Exemplary Formulations

The following Tables provide non-limiting examples of various hydrogel formulations that include thermolysin and a cellulosic ether.

TABLE 1

Figure 2:
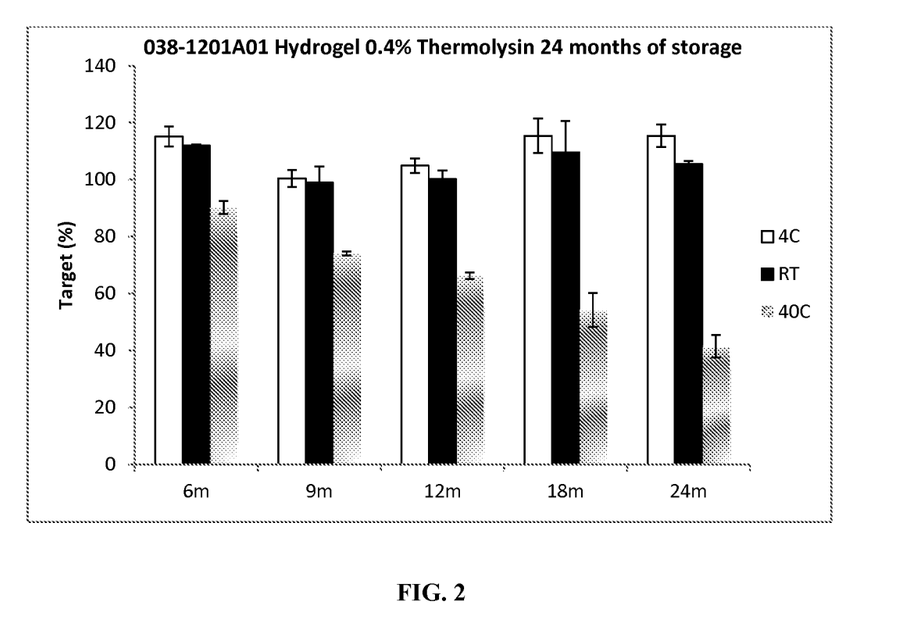
FIG. 2. A graph showing thermolysin activity expressed as % Target over 24 months when thermolysin is provided in an aqueous hydrogel of the present invention and stored at 4° C., room temperature (20-25° C.), and 40° C. The formulation used in FIG. 2 is provided in Table 1.

Thermolysin/HEC Hydrogel (in FIG. 2)

| Ingredient | % Concentration (by weight) |
| --- | --- |
| Hydroxyethylcellulose (HEC) | 2.68 |
| NaCl | 0.28 |
| CaCl$_2$ | 0.11 |
| Propylene Glycol | 14.2 |
| Methyl Paraben | 0.24 |
| Propyl Paraben | 0.05 |
| Thermolysin | 0.3917 |
| Tris buffer (10 mM, pH 7.5) | q.s. |
| Total | 100 |

Process: HEC used was Natrosol ® 250 Pharm from Ashland (USA). The buffer used was Tris buffer (10 mM, pH 7.5). The hydrogel was prepared by mixing propylene glycol and preservatives (e.g., methyl and propyl paraben) in Tris Buffer at 70° C. Upon solubilization (i.e., clear solution is obtained), the solution is cooled to room temperature (RT) and gelling agent (HEC) was added. The mixture is stirred until homogeneous (i.e., no visible particles of gelling agent, HEC), a hydrogel is formed. The active phase is made by mixing thermolysin, NaCl and CaCl$_2$ in DI water or Tris buffer (pH = 7.5) at appropriate concentration. Upon homogenization (a white slurry will be obtained), the active phase is added to a hydrogel (at appropriate concentration). The final mixture is stirred for at least 2 h at RT. Milky hydrogel is obtained having an average viscosity of 54,876 cps (standard deviation of 251.66, and based on three separate measurements from three samples of same hydrogel), as measured on a Brookfield Viscometer at 10 rpm, spindle #14, RT, 30 sec. Thermolysin was stable in this formulation for 6 months, 12 months, 18 months and 24 months at room temperature and 4° C. as measured by Casein digestion method.

TABLE 2

Figure 3:
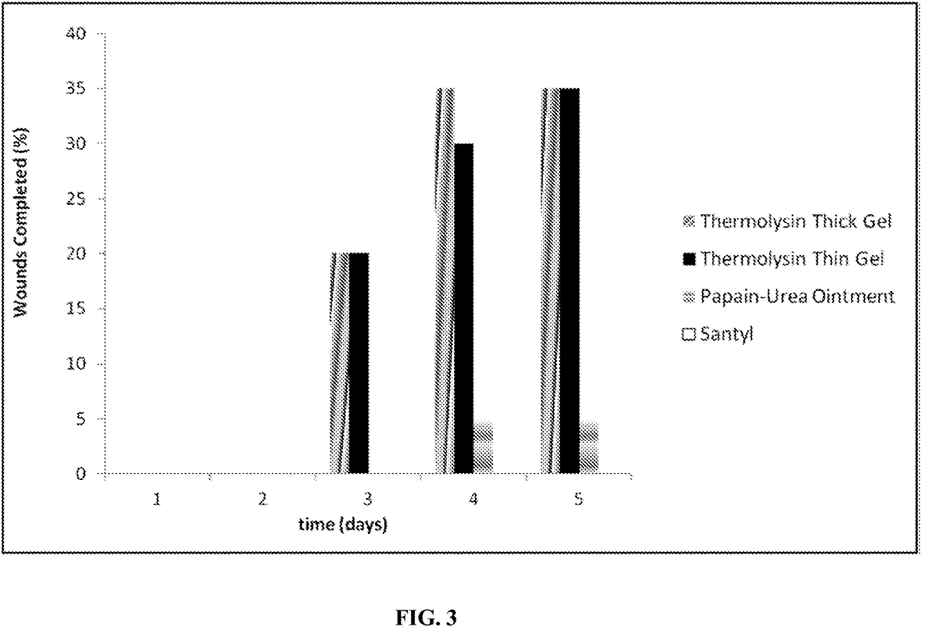
FIG. 3. A graph showing the percentage debridement in pig eschar wounds over time following treatment with SANTYL® collagenase ointment, a papain/urea ointment (with 2.5% papain and 10% urea), a thin (~50,000 cps) thermolysin aqueous hydrogel of the present invention, and a thick (~70,000 cps) thermolysin aqueous hydrogel of the present invention. The formulations for the thin and thick hydrogels are provided in Tables 2 and 3, respectively.

Thermolysin/HEC Hydrogel ("Thin Gel" in FIG. 3)

| Ingredient | % Concentration (by weight) |
| --- | --- |
| Hydroxyethylcellulose (HEC) | 3 |
| NaCl | 0.28 |
| CaCl$_2$ | 0.11 |
| Propylene Glycol | 14.9 |
| Methyl Paraben | 0.25 |
| Propyl Paraben | 0.05 |
| Thermolysin | 0.795 |
| Tris buffer (10 mM, pH 7.5) | q.s. |
| Total | 100 |

Process: HEC used was Natrosol ® 250 Pharm from Ashland (USA). The buffer used was Tris buffer (10 mM, pH 7.5). The hydrogel was prepared by mixing propylene glycol and preservatives (e.g., methyl and propyl paraben) in Tris buffer at 70° C. Upon solubilization (i.e., clear solution is obtained), the solution is cooled to room temperature (RT) and gelling agent (HEC) was added. The mixture is stirred until homogeneous (i.e., no visible particles of gelling agent, HEC), a hydrogel is formed. The active phase is made by mixing thermolysin, NaCl and CaCl$_2$ in DI water or Tris buffer (pH = 7.5) at appropriate concentration. Upon homogenization (a white slurry will be obtained), the active phase is added to a hydrogel (at appropriate concentration). The final mixture is stirred for at least 2 h at RT. Milky hydrogel is obtained having an average viscosity of 64,900 cps (standard deviation of 173.21 based on three separate measurements from three samples of same hydrogel), as measured on a Brookfield Viscometer at 10 rpm, spindle #14, RT, 30 sec.

TABLE 3

Thermolysin/HEC Hydrogel ("Thick Gel" in FIG. 3)

| Ingredient | % Concentration (by weight) |
| --- | --- |
| Hydroxyethylcellulose (HEC) | 4 |
| NaCl | 0.28 |
| CaCl$_2$ | 0.11 |
| Propylene Glycol | 14.77 |
| Methyl Paraben | 0.25 |
| Propyl Paraben | 0.05 |
| Thermolysin | 0.797 |
| Tris buffer (10 mM, pH 7.5) | q.s. |
| Total | 100 |

Process: HEC used was Natrosol ® 250 Pharm from Ashland (USA). The buffer used was Tris buffer (10 mM, pH 7.5). The hydrogel was prepared by mixing propylene glycol and preservatives (e.g., methyl and propyl paraben) in Tris buffer at 70° C. Upon solubilization (i.e., clear solution is obtained), the solution is cooled to room temperature (RT) and gelling agent (HEC) was added. The mixture is stirred until homogeneous (i.e., no visible particles of gelling agent, HEC), a hydrogel is formed. The active phase is made by mixing thermolysin, NaCl and CaCl$_2$ in DI Water or Tris buffer (pH = 7.5) at appropriate concentration. Upon homogenization (a white slurry will be obtained), the active phase is added to a hydrogel (at appropriate concentration). The final mixture is stirred for at least 2 h at RT. Milky hydrogel is obtained having an average viscosity of 170,067 cps (standard deviation of 25,516, and based on three separate measurements from three samples of same hydrogel), as measured on a Brookfield Viscometer at 5 rpm, spindle #14, RT, 60 sec.

TABLE 4

Thermolysin/HPMC Hydrogel

| Ingredient | % Concentration (by weight) |
| --- | --- |
| Hydroxymethylpropylcellulose (HPMC) | 1.05 |
| Propylene Glycol | 20.17 |
| Methyl Paraben | 0.27 |
| Propyl Paraben | 0.05 |
| Thermolysin | 0.202 |
| DI Water | q.s. |
| Total | 100 |

Process: HPMC used was Methocel K-15M from DOW (USA). The suspending media was DI water. The hydrogel was prepared by mixing propylene glycol and preservatives (e.g., methyl and propyl paraben) in Tris buffer at 70° C. Upon solubilization (i.e., clear solution is obtained), the solution is cooled to room temperature (RT) and gelling agent (HPMC) was added. The mixture is stirred until homogeneous (i.e., no visible particles of gelling agent, HPMC), a hydrogel is formed. The active phase is made by mixing thermolysin, in DI water at appropriate concentration. Upon homogenization (a white slurry will be obtained), the active phase is added to a hydrogel (at appropriate concentration). The final mixture is stirred for at least 2 h at RT. Milky hydrogel is obtained having an average viscosity of 9,400 cps (standard deviation of 100, and based on three separate measurements from three samples of same hydrogel), as measured on a Brookfield Viscometer at 10 rpm, spindle #14, RT, 30 sec. Thermolysin was stable in this formulation for 10 months at room temperature and 4° C. as measured by Casein digestion method.

TABLE 5

Thermolysin/HPC Hydrogel

| Ingredient | % Concentration (by weight) |
| --- | --- |
| Hydroxypropylcellulose (HPC) | 1.55 |
| Glycerin | 3.41 |
| Phenoxyethanol | 0.73 |
| Thermolysin | 0.205 |
| NaCl | 0.82 |
| DI Water (10% PBS pH = 7.5) | q.s. |
| Total | 100 |

Process: HPC (Klucel ™) used was from Ashland Inc. (USA). The suspending media was DI water. The hydrogel was prepared by mixing glycerin, phenoxy ethanol and gelling agent (HPC) in DI water at RT. Upon solubilization a hydrogel was formed. The active phase is made by mixing thermolysin and NaCl, in DI eater at appropriate concentration. Upon homogenization (a white slurry will be obtained), the active phase is added to a hydrogel (at appropriate concentration). The final mixture is stirred for at least 2 h at RT. Milky hydrogel is obtained having an average viscosity of 42,633 cps (standard deviation of 1,205.5, and based on three separate measurements from three samples of same hydrogel), as measured on a Brookfield Viscometer at 10 rpm, spindle #14, RT, 30 sec. Thermolysin was stable in this formulation for 10 months at room temperature and 4° C. as measured by Casein digestion method.

TABLE 6

Thermolysin/Carbopol 940 Hydrogel

| Ingredient | % Concentration (by weight) |
| --- | --- |
| Carbopol 940 | 0.56 |
| Thermolysin | 0.1 |
| 1M NaOH | 10 |
| Tris Buffer (10 mM, pH = 7.5) | q.s. |
| Total | 100 |

Process: Carbopol 940 used was obtained from Lubrizol (USA). The suspending media was Tris buffer (10 mM, pH = 7.5). The hydrogel was prepared by mixing gelling agent (Carbopol 940) in Tris buffer at RT. Upon solubilization a blurry solution was formed. The hydrogel was formed upon the neutralization of the solution with 1M NaOH. The active phase is made by mixing thermolysin in Tris buffer at appropriate concentration. The active phase was added to a hydrogel. The final mixture is stirred for at least 2 h at RT. Milky hydrogel is obtained. Thermolysin activity was inhibited in this formulation as measured by Casein digestion method.

TABLE 7

Thermolysin/Polyquaternium-10 Hydrogel

| Ingredient | % Concentration (by weight) |
| --- | --- |
| Polyquaternium-10 | 1.49 |
| Thermolysin | 0.104 |
| Tris Buffer (10 mM, pH = 7.5) | q.s. |
| Total | 100 |

Process: Polyquaternium-10 (U-Care Polymer JR-30M) used was from DOW (USA). The suspending media was Tris buffer (10 mM, pH = 7.5). The hydrogel was prepared by mixing gelling agent (Polyquaternium-10) in Tris buffer at RT. Upon solubilization a hydrogel was formed. The active phase is made by mixing Thermolysin in Tris buffer at appropriate concentration. The active phase was added to a hydrogel. The final mixture is stirred for at least 2 h at RT. Milky hydrogel is obtained. Thermolysin was unstable in this formulation. About 60% loss in the activity was measured after 1 month storage at room temperature by Casein digestion method.

TABLE 8

Thermolysin/Hispagel Hydrogel

| Ingredient | % Concentration (by weight) |
| --- | --- |
| Hispagel-200 | 43.8 |
| Thermolysin | 0.106 |
| 1M NaOH | 6.56 |
| Tris Buffer (10 mM, pH = 7.5) | q.s. |
| Tris Buffer Solid | 1.01 |
| Total | 100 |

Process: Hispagel-200 used was obtained from Cognis (USA). The suspending media was Tris buffer (10 mM, pH = 7.5). The hydrogel was prepared by mixing gelling agent (Hispagel-200) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. The final pH was adjusted by 1M NaOH and solid Tris buffer. Milky hydrogel is obtained. Thermolysin activity was inhibited in this formulation as measured by Casein digestion method.

TABLE 9

Thermolysin/Aristoflex Hydrogel

| Ingredient | % Concentration (by weight) |
| --- | --- |
| Aristoflex AVC | 0.96 |
| Thermolysin | 0.1 |
| Tris Buffer (10 mM, pH = 7.5) | q.s. |
| Total | 100 |

Process: Aristoflex AVC used was from Clariant (USA). The suspending media was Tris buffer (10 mM, pH = 7.5). The hydrogel was prepared by mixing gelling agent (Aristoflex AVC) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin activity was inhibited in this formulation as measured by Casein digestion method.

TABLE 10

Thermolysin/Ultragel-300 Hydrogel

| Ingredient | % Concentration (by weight) |
| --- | --- |
| Ultragel-300 | 0.55 |
| Thermolysin | 0.1 |
| Tris Buffer (10 mM, pH = 7.5) | q.s. |
| Total | 100 |

Process: Ultragel-300 (polyquaternium-37) used was obtained from Cognis (USA). The suspending media was Tris buffer (10 mM, pH = 7.5). The hydrogel was prepared by mixing gelling agent (Ultragel-300) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin was unstable in this formulation. About 80% loss in the activity was measured after 1 month storage at room temperature by Casein digestion method.

TABLE 11

Thermolysin/Gellan Gum Hydrogel

| Ingredient | % Concentration (by weight) |
| --- | --- |
| Gellan Gum | 0.2454 |
| Thermolysin | 0.101 |
| Tris Buffer (10 mM, pH = 7.5) | q.s. |
| Total | 100 |

Process: Gelan gum used was obtained from C.P. Kelco (USA). The suspending media was Tris buffer (10 mM, pH = 7.5). The hydrogel was prepared by mixing gelling agent (Gelan gum) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin was unstable in this formulation. About 50% loss in the activity was measured after 1 month storage at room temperature by Casein digestion method.

TABLE 12

Thermolysin/Cosmedia Guar Hydrogel

| Ingredient | % Concentration (by weight) |
| --- | --- |
| Cosmedia Guar | 1.217 |
| Thermolysin | 0.102 |
| Tris Buffer (10 mM, pH = 7.5) | q.s. |
| Total | 100 |

Process: Cosmedia guar (guar hydroxypropyltrimonium chloride) used was obtained from Cognis (USA). The suspending media was Tris buffer (10 mM, pH = 7.5). The hydrogel was prepared by mixing gelling agent (Cosmedia Guar) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin was unstable in this formulation. About 60% loss in the activity was measured after 1 month storage at room temperature by Casein digestion method.

TABLE 13

Thermolysin/Xanthan Gum Hydrogel

| Ingredient | % Concentration (by weight) |
| --- | --- |
| Xanthan Gum | 1.5 |
| Thermolysin | 0.102 |
| Tris Buffer (10 mM, pH = 7.5) | q.s. |
| Total | 100 |

Process: Xanthan gum used was obtained from TIC Gums (USA). The suspending media was Tris buffer (10 mM, pH = 7.5). The hydrogel was prepared by mixing gelling agent (xanthan gum) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin was unstable in this formulation. About 70% loss in the activity was measured after 1 month storage at room temperature by Casein digestion method.

TABLE 14

Thermolysin/CMC Ticalose Hydrogel

| Ingredient | % Concentration (by weight) |
|---|---|
| CMC Ticalose (Sodium) | 2.03 |
| Thermolysin | 0.102 |
| Tris Buffer (10 mM, pH = 7.5) | q.s. |
| Total | 100 |

Process: CMC Ticalose (sodium carboxymethylcellulose - anionic) used was obtained from TIC Gums (USA). The suspending media was Tris buffer (10 mM, pH = 7.5). The hydrogel was prepared by mixing gelling agent (CMC Ticalose) in Tris buffer at RT. Upon solubilization a hydrogel was formed. The active phase is made by mixing thermolysin in Tris buffer at appropriate concentration. The active phase was added to a hydrogel. The final mixture is stirred for at least 2 h at RT. Milky hydrogel is obtained. Thermolysin activity was inhibited in this formulation.

TABLE 15

Thermolysin/PolyOx WSR Hydrogel

| Ingredient | % Concentration (by weight) |
|---|---|
| PolyOx WSR | 2 |
| Thermolysin | 0.1 |
| Tris Buffer (10 mM, pH = 7.5) | q.s. |
| Total | 100 |

Process: PolyOx (PEG) WSR used was obtained from TIC Gums (USA). The suspending media was Tris buffer (10 mM, pH = 7.5). The hydrogel was prepared by mixing gelling agent (PolyOx WSR) in Tris buffer at RT. Upon solubilization a hydrogel/thick liquid was formed. The active phase is made by mixing Thermolysin in Tris buffer at appropriate concentration. The active phase was added to a hydrogel. The final mixture is stirred for at least 2 h at RT. Milky hydrogel/thick liquid is obtained. Thermolysin was unstable in this formulation. About 80% loss in the activity was measured after 1 month storage at room temperature by Casein digestion method.

TABLE 16

Thermolysin/Oil-in-Water Emulsion Cream

| Ingredient | % Concentration (by weight) |
|---|---|
| Emulsifying Wax | 11 |
| Thermolysin | 0.2 |
| Isopropyl Myristate | 4 |
| 1% $KH_2PO_4$ (pH = 7.5) | q.s. |
| Glycerin | 5 |
| Methyl paraben | 0.2 |
| Propyl Paraben | 0.08 |
| Total | 100 |

Process: Emulsifying Wax (Polowax) was obtained from Croda (USA). The suspending media was $KH_2PO_4$ (1%, w/w, pH = 7.5). The creaml was prepared by Solubilizing Glycerin and preservatives in buffer at 70 C. Upon solubilization (clear solution) emulsifying agent (Emusifying Wax) and Oil (Isopropyl Myristate) were added. Upon mixing (1 h at 70 C.), the mixture was cooled to RT. Milky white cream was obtained. Thermolysin was found unstable in this formulation after 4 months at room temperature as measured by Casein digestion method.

TABLE 17

Thermolysin/Carbopol Aqua SF-1 Hydrogel

| Ingredient | % Concentration (by weight) |
|---|---|
| Carbopol Aqua SF-1 | 8.53 |
| Thermolysin | 0.2 |
| 1M NaOH | 10 |
| DI Water | q.s. |
| Methyl Paraben | 0.19 |
| Propyl Paraben | 0.08 |
| Glycerin | 4.8 |
| Total | 100 |

Process: Carbopol Aqua SF-1 used was obtained from Lubrizol (USA). The suspending media was DI Water. The hydrogel was prepared by mixing gelling agent (Carbopol Aqua SF-1) in DI Water along with preservatives and Glycerin at 70 C. Upon solubilization the solution was cooled to RT. The hydrogel was formed upon the neutralization of the solution with 1M NaOH. The active phase is made by mixing Thermolysin in DI Water at appropriate concentration. The active phase was added to a hydrogel. The final mixture is stirred for at least 2 h at RT. Translucent hydrogel was obtained. Thermolysin activity was inhibited in this formulation.

TABLE 18

Thermolysin/Poloxamer-407 based Hydrogel

| Ingredient | % Concentration (by weight) |
|---|---|
| Poloxamer-407 | 18 |
| Thermolysin | 0.2 |
| 1% $KH_2PO_4$ | q.s. |
| Phenoxy Ethanol | 0.53 |
| Total | 100 |

Process: Poloxamer-407 used was obtained from BASF (USA). The suspending media was 1% $KH_2PO_4$ Buffer. The hydrogel was prepared by mixing gelling agent (Poloxamer-407) in buffer along with preservatives at 4 C.. Upon solubilization the solution was equilibrated to RT. The hydrogel was formed upon temperature from 4 C. to RT. Clear hydrogel was obtained. Thermolysin activity was inhibited in this formulation.

TABLE 19

Thermolysin/Poloxamers based hydrophilic dispersion

| Ingredient | % Concentration (by weight) |
|---|---|
| Poloxamer-407 | 15 |
| Thermolysin | 0.2 |
| Poloxamer-124 | q.s. |
| Poloxamer-188 | 6 |
| Total | 100 |

Process: Poloxamer-407/Poloxamer-124 and Poloxamer-188 used were obtained from BASF (USA). The dispersion was made by heating and mixing the Poloxamers at 70 C. until homogeneous. The active phase was prepared by suspending the enzyme in Poloxamer-124 and adding it to a previously cooled (to RT) main phase. White cream was obtained. Thermolysin was found unstable in this formulation after 6 months at room temperature as measured by Casein digestion method.

Example 2

Thermolysin Stability Data

The stability of thermolysin in the Table 1 Thermolysin/HEC hydrogel was tested over a one-month period while being stored at room temperature (20 to 25° C.). For comparison purposes, various thermolysin hydrogels were also prepared with gelling agents other than nonionic cellulose ethers. Such gelling agents included polyquarternium-10, Ultragel 300, gellan gum, cosmedia guar, xanthan gum, anionic cellulose ether, Carbopols, polaxamers, polyox WSR, and others. The additional hydrogels were also stored at room temperature (20 to 25° C.).

Figure 1:
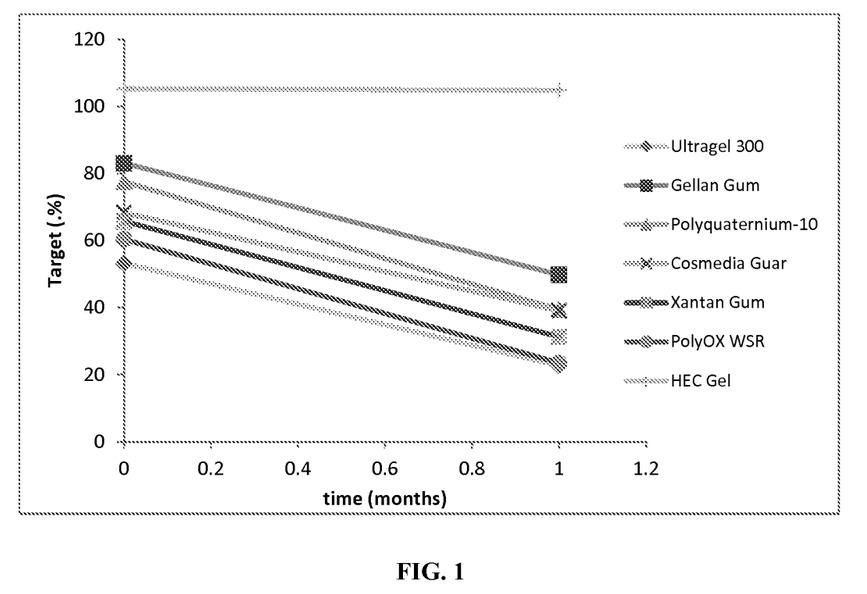
FIG. 1. A graph showing 1 month thermolysin activity expressed as % Target in a hydrogel of the present invention (HEC) and in hydrogels that do not include a nonionic cellulose ether.

FIG. 1 provides a summary of the stability results. The thermolysin activity in hydrogels (e.g., HEC hydrogel) might be slightly different than the expected activity, due to favorable or unfavorable influence of the formulation excipients on enzyme activity.

Data presented in FIG. 1 suggest that, surprisingly, the thermolysin activity for the Table 1 Thermolysin/HEC hydrogel remained the same/did not decrease over the one-month storage period. By comparison, the thermolysin activity in hydrogels that did not include a nonionic cellulose ether gelling agent decreased substantially over this period (over 50% decrease in activity). Without wishing to be bound by theory, it is thought that the nonionic structure and weak amphiphilic (i.e., both polar and non-polar parts of the cellulose ethers) character of cellulose ethers as the gelling agent for the hydrogel creates an environment that favors the stability of thermolysin.

A further stability study was performed on each of the hydrogels exemplified in Tables 1, 4, and 5 and compared with various thermolysin formulations ranging from a cream (oil-in-water emulsion), anhydrous gel (poloxamer), hydrogels (polyacrylate-Carbopol) and various other hydrogel bases (e.g., polyquarternium-10). The results of this study are provided in descriptions of Tables 1 and 4-19. Tables 1, 4, and 5, which are non-limiting hydrogels of the present invention, are superior over all of the other tested thermolysin formulations. The initial activity for these other formulas was less than 85% of the targeted amount, and some were even 0% of the targeted amount initially.

The method used to determine thermolysin activity (stability) for the hydrogels in Tables 1 and 4-19 is the Casein Digestion Method: Thermolysin activity is determined by measuring the absorbance increase of digested Casein fragments upon digestion relative to the reference standard. The thermolysin hydrogel (250 mg), was solubilized in 25 ml of TBS buffer (50 mM Tris, 100 mM NaCl, 13.5 mM $CaCl_2$, pH=7.4). Upon solubilization, the solution is diluted 1:10 using TBS. The Standard solutions were prepared using the Thermolysin raw material and TBS, prepared in a series of concentrations. The substrate was a Casein solution (2 g in 100 ml of Phosphate Buffer 50 mM $Na_2HPO_4$). The digestion procedure was as follows: 2.5 ml of Casein solution, 1.0 ml of analyte or standard were incubated in water bath at 37° C. for 30 min. Upon digestion, the stop solution, 1.5 ml Trichloroacetic acid (TCA, 30 g in 80 ml of DI water) was added. The blank solution was made as follows: 2.5 ml Casein solution, 1.5 ml of TCA and 1.0 ml of analyte or standard (added after TCA). Samples were left at 37° C. for 45 min., followed by filtration through 0.45 um nylon filter and analysis at 280 nm spectrophotometrically.

The standard curve of thermolysin was calculated by using third order polynomial curve fitting. The amount of thermolysin in each formulation at different storage conditions is calculated using the standard curve.

The % Target was calculated by:

% Target=(Tested activity units/g of formulation)
*100/(Tested activity units of thermolysin standard in mg*Thermolysin concentration in the formulation, mg/g).

FIG. 2 provides an additional thermolysin stability assay, in which the hydrogel from Table 1 was tested and subjected to storage conditions ranging from 4° C., room temperature (20 to 25° C.), and 40° C. for 6 months, 9 months, 12 months, 18 months and 24 months. The hydrogel was stable at room temperature as indicated by a decrease of activity less than 20% at 6 months, 9 months, 12 months, 18 months and 24 months (i.e., retained at least 80% activity). Similarly, the hydrogel was stable for 24 months after storage at 4° C. Approximately 55-60% of the thermolysin remained stable when stored at an elevated temperature of 40° C. for 18 months and 40% of the thermolysin remained stable when stored at an elevated temperature of 40° C. for 24 months—this equates to long-term shelf life/room temperature storage conditions of the hydrogel, as elevated temperatures are used to confirm the shelf life stability of a given product over a shorter testing period. This also explains the increasing loss of stability at 24 months when stored at 40° C.

Example 3

In Vivo Debridement of Pig Burn Wounds

The hydrogels in Tables 2 and 3 were evaluated for efficacy in debriding burn wounds in pigs. In this in vivo study, burn wounds were generated on the backs of pigs. Pigs were anesthetized, and the torso was shaved with clippers and a razor and washed with vedadine. Then an isopropyl rinse was performed to sterilize the surgical field. Twenty 2-cm wounds were created on the dorsum of each pig. The wounds were created using solid brass rods, heated to 100° C. in sand baths, held on the skin for 45 seconds. The wounds were left to dry for five days, giving the eschars time to form, with protective foam dressings being replaced every other day during eschar formation. After eschar formation and on a daily basis for treatments, the wounds were cleaned with saline, photographed, treated according to the treatment scheme, and dressed with non-adherent dressings (pre-moistened with saline) secured with Transpore tape and occlusive secondary dressings. Statistical significance for the number of eschars fully debrided was determined using Fisher's Exact test.

Following eschar formation, all wounds were treated once a day with either: a papain/urea ointment (with 2.5% papain and 10% urea); SANTYL collagenase ointment; a thin thermolysin hydrogel (Table 2.); a thick thermolysin hydrogel (Table 3.); or a hydrogel placebo (i.e., a hydrogel lacking thermolysin). As shown in FIG. 3, 20% of the wounds were fully debrided after three days of treatment with the Table 2 and 3 thermolysin hydrogels. At the three day time point, no wounds were fully debrided following treatment with papain/urea ointment or SANTYL collagenase ointment. After four or five days, 30-35% of the wounds were fully debrided following treatment with the Table 2 and 3 thermolysin hydrogels, while only 5% of the wounds were fully debrided following treatment with papain/urea ointment. No wounds were fully debrided following five days of treatment with SANTYL collagenase ointment.

The invention claimed is:
1. A hydrogel comprising:
(a) a hydrophilic gelling agent that includes a nonionic cellulose ether; and
(b) active thermolysin,
wherein the proteolytic activity of the thermolysin does not decrease by more than 20% when stored at room temperature for 6 months,
wherein the hydrogel further comprises a preservative and/or is sterile,
wherein the nonionic cellulose ether is hydroxyethylcellulose, hydroxypropylcellulose, or the combination thereof, and
wherein the hydrogel has a viscosity of 15,000 to 100,000 cps, as measured with a Brookfield RV Viscometer, spindle 14 with small sample adapter, at 10 rpm at room temperature read at 30 seconds.
2. The hydrogel of claim 1, wherein the proteolytic activity of the thermolysin does not decrease by more than 10% when stored at room temperature for 6 months.

3. The hydrogel of claim 1, wherein the proteolytic activity of the thermolysin does not decrease by more than 10% when stored at room temperature for 24 months.

4. The hydrogel of claim 1, wherein the nonionic cellulose ether comprises hydroxyethylcellulose, and wherein the hydrogel comprises 2.5 to 4.5% w/w of the hydroxyethylcellulose.

5. The hydrogel of claim 1, wherein the nonionic cellulose ether comprises hydroxypropylcellulose, and wherein the hydrogel comprises 0.01 to 10% w/w of the hydroxypropylcellulose.

6. The hydrogel of claim 1, comprising 0.5 to 1% w/w/ of the thermolysin.

7. The hydrogel of claim 1, comprising 0.1 to 5% w/w of the thermolysin.

8. The hydrogel of claim 1, further comprising a buffer having a pH of 7.0 to 8.0.

9. The hydrogel of claim 8, wherein the hydrogel comprises a buffer having a pH of about 7.5.

10. The hydrogel of claim 1, wherein the hydrogel further comprises a metal salt.

11. The hydrogel of claim 10, wherein the metal salt is sodium chloride or calcium chloride or mixtures thereof.

12. The hydrogel of claim 1, wherein the preservative is methylparaben, propylparaben, or phenoxyethanol, or mixtures thereof.

13. The hydrogel of claim 1, wherein the thermolysin is solubilized within the hydrogel.

14. The hydrogel of claim 1, wherein the thermolysin is suspended within the hydrogel.

15. The hydrogel of claim 1, wherein the thermolysin is partially solubilized and partially suspended within the hydrogel.

16. A method of debriding a wound comprising topically applying a composition according to claim 1 to a wound in need of debridement.

17. The method of claim 16, wherein the wound is a chronic wound.

18. The method of claim 17, wherein the chronic wound is a diabetic foot ulcer, a venous leg ulcer, an arterial leg ulcer, a decubitus ulcer, a stasis ulcer, a dermal ulcer, a burn, or a pressure ulcer.

19. The method of claim 16, wherein the wound includes necrotic tissue.

20. The method of claim 19, wherein the necrotic tissue is an eschar.

21. A method for stabilizing thermolysin comprising preparing a hydrogel according to claim 1.

* * * * *